(12) United States Patent
Woods et al.

(10) Patent No.: US 10,653,397 B2
(45) Date of Patent: May 19, 2020

(54) VIAL USEABLE IN TISSUE EXTRACTION PROCEDURES

(71) Applicant: Gallant Pet, Inc., La Jolla, CA (US)

(72) Inventors: Erik J. Woods, Indianapolis, IN (US); Shelly J. Zacharias, Indianapolis, IN (US)

(73) Assignee: Gallant Pet, Inc., La Jolla, CA (US)

( * ) Notice: Subject to any disclaimer, the term of this patent is extended or adjusted under 35 U.S.C. 154(b) by 0 days.

(21) Appl. No.: 15/388,145

(22) Filed: Dec. 22, 2016

(65) Prior Publication Data

US 2017/0100104 A1    Apr. 13, 2017

Related U.S. Application Data

(63) Continuation of application No. 13/571,044, filed on Aug. 9, 2012, now Pat. No. 9,549,715.

(60) Provisional application No. 61/521,625, filed on Aug. 9, 2011.

(51) Int. Cl.

| | |
|---|---|
| *A61B 10/00* | (2006.01) |
| *A61B 10/02* | (2006.01) |
| *B01L 3/00* | (2006.01) |
| *G01N 1/08* | (2006.01) |
| *G01N 1/31* | (2006.01) |
| *B65D 51/00* | (2006.01) |
| *B65D 51/24* | (2006.01) |

(52) U.S. Cl.
CPC ...... *A61B 10/0096* (2013.01); *A61B 10/0233* (2013.01); *B01L 3/50825* (2013.01); *B65D 51/002* (2013.01); *B65D 51/24* (2013.01); *G01N 1/08* (2013.01); *G01N 1/31* (2013.01); *B01L 2300/046* (2013.01); *B01L 2300/0672* (2013.01)

(58) Field of Classification Search
CPC .. A61B 10/0096; A61B 10/0233; G01N 1/08; G01N 1/31; B01L 3/50825; B01L 2300/046
See application file for complete search history.

(56) References Cited

U.S. PATENT DOCUMENTS

| | | | |
|---|---|---|---|
| 3,753,432 A | | 8/1973 | Guerra |
| 3,995,772 A | | 12/1976 | Liautaud |
| 4,376,634 A | | 3/1983 | Prior et al. |
| 5,268,148 A | * | 12/1993 | Seymour ............ A61B 10/0051 422/401 |
| 5,360,410 A | | 11/1994 | Wacks |
| 5,388,588 A | | 2/1995 | Nabai et al. |
| 5,467,780 A | | 11/1995 | Nabai et al. |

(Continued)

FOREIGN PATENT DOCUMENTS

| | | | | |
|---|---|---|---|---|
| DE | 2903760 B | * | 6/1980 | ............ A61B 10/00 |
| DE | 2903760 B1 | | 6/1980 | |

(Continued)

*Primary Examiner* — Sean P Dougherty
(74) *Attorney, Agent, or Firm* — Knobbe, Martens, Olson & Bear, LLP (57) ABSTRACT

Disclosed is a device useful for preserving tissue samples after extraction from human or animal patients. The device includes a circular blade for taking a tissue sample, the blade being coupled to a sealing cap which mates to one end of a container. A retrieval port is also disclosed for extracting fluids from the container. Methods are also disclosed by which tissue samples may be taken and prepared for storage, processing, culture, or other analysis.

8 Claims, 4 Drawing Sheets

(56) References Cited

U.S. PATENT DOCUMENTS

| | | | |
|---|---|---|---|
| 5,478,337 A | 12/1995 | Okamoto et al. | |
| 5,514,097 A | 5/1996 | Knauer | |
| 5,533,518 A | 7/1996 | Vogler | |
| 5,578,459 A | 11/1996 | Gordon et al. | |
| 5,653,694 A * | 8/1997 | Powles | A61B 10/0283 604/240 |
| 5,701,910 A * | 12/1997 | Powles | A61B 10/0283 600/577 |
| 5,746,724 A * | 5/1998 | Powles | A61B 10/0283 600/565 |
| 5,827,199 A | 10/1998 | Alexander | |
| 5,902,280 A * | 5/1999 | Powles | A61B 10/0283 600/577 |
| 6,145,688 A * | 11/2000 | Smith | B01L 3/50825 215/278 |
| 6,440,373 B1 * | 8/2002 | Gomes | B01L 3/508 422/547 |
| 6,537,257 B1 * | 3/2003 | Wien | A61M 5/3202 604/198 |
| 6,659,338 B1 * | 12/2003 | Dittmann | A01K 11/003 235/375 |
| 6,979,307 B2 | 12/2005 | Beretta et al. | |
| 7,387,216 B1 | 6/2008 | Smith | |
| 7,456,024 B2 | 11/2008 | Dahm et al. | |
| 7,674,434 B2 | 3/2010 | Sakal et al. | |
| 7,745,106 B2 | 6/2010 | Grippi et al. | |
| 7,886,779 B2 | 2/2011 | Smith | |
| 8,517,957 B2 * | 8/2013 | Decaluwe | A01K 11/003 600/567 |
| 8,652,802 B2 * | 2/2014 | Rutty | G01N 1/04 435/40.5 |
| 8,763,287 B2 * | 7/2014 | Hilpert | A01K 11/003 119/655 |
| 9,029,138 B2 * | 5/2015 | Groelz | G01N 1/36 435/325 |
| 9,549,715 B2 * | 1/2017 | Woods | A61B 10/0096 |
| 9,554,557 B2 * | 1/2017 | Nehls | A01K 11/003 |
| 2002/0038111 A1 | 3/2002 | Alchas et al. | |
| 2002/0169408 A1 | 11/2002 | Beretta et al. | |
| 2003/0028172 A1 | 2/2003 | Epstein et al. | |
| 2003/0109832 A1 | 6/2003 | Rindlisbacher | |
| 2004/0019295 A1 | 1/2004 | Zhou et al. | |
| 2004/0071786 A1 | 4/2004 | Grippi et al. | |
| 2005/0209568 A1 | 9/2005 | Shanley | |
| 2005/0228310 A1 * | 10/2005 | Pfistershammer | B01L 11/002 600/567 |
| 2006/0245977 A1 * | 11/2006 | Bodner | A61B 10/0045 422/400 |
| 2007/0009490 A1 | 1/2007 | Conte et al. | |
| 2007/0021684 A1 | 1/2007 | Brielmeier et al. | |
| 2007/0148106 A1 | 6/2007 | Wertz et al. | |
| 2007/0270710 A1 | 11/2007 | Frass et al. | |
| 2008/0044313 A1 * | 2/2008 | Caisley | A01K 11/003 422/400 |
| 2008/0121050 A1 | 5/2008 | Sakal et al. | |
| 2008/0190857 A1 | 8/2008 | Beretta et al. | |
| 2008/0228163 A1 | 9/2008 | Smith | |
| 2009/0112119 A1 | 4/2009 | Kim | |
| 2009/0193880 A1 * | 8/2009 | Halverson | G01N 1/18 73/64.56 |
| 2010/0248215 A1 | 9/2010 | Halverson et al. | |
| 2010/0255484 A1 | 10/2010 | Halverson et al. | |
| 2010/0280414 A1 | 11/2010 | Haywood et al. | |
| 2011/0212002 A1 * | 9/2011 | Curry | B01L 3/5029 422/430 |
| 2011/0275955 A1 | 11/2011 | Lee et al. | |
| 2011/0282240 A1 | 11/2011 | Al Mohizea | |
| 2012/0010526 A1 * | 1/2012 | Hilpert | A01K 11/003 600/564 |
| 2012/0037563 A1 * | 2/2012 | Liao | A61B 10/0038 210/634 |
| 2017/0336400 A1 * | 11/2017 | Meng | A61B 10/007 |

FOREIGN PATENT DOCUMENTS

| | | | |
|---|---|---|---|
| DE | 10144127 C1 * | 2/2003 | ......... A61B 10/0096 |
| JP | 10192364 | 7/1998 | |
| JP | 2011/001114 A | 1/2011 | |

* cited by examiner

VIAL USEABLE IN TISSUE EXTRACTION PROCEDURES

CROSS-REFERENCE TO RELATED APPLICATIONS

This application is a Continuation of U.S. Ser. No. 13/571,044 filed on Aug. 9, 2012, which claims the benefit of U.S. Provisional Patent Application Ser. No. 61/521,625 filed Aug. 9, 2011, which is incorporated herein by reference in its entirety.

BACKGROUND

The present invention relates to a device for extraction, collection, transport, processing and preservation of a living tissue sample.

Certain therapies utilize stem cells for the treatment of diseases and conditions in humans and animals. Optimally the stem cells are obtained from the patient, cultured and processed for storage. Many stem cell based therapies require a large number of viable cells. Procedures for culturing and preserving a desired population of stem cells have been well refined over the years. However, one common problem that remains is in collecting the cells and transporting them to another location for culturing.

SUMMARY

The embodiments disclosed are directed to tissue extraction and collection devices and methods of using such devices to preserve and retrieve collected samples. The disclosed embodiments include vials having containers and accompanying blades attached to the container caps which are useful together to collect a tissue sample and maintain it for later testing, culturing, processing, or storage.

Further, still additional embodiments will be apparent to those skilled in the art from the Detailed Description herein.

DETAILED DESCRIPTION

For the purpose of promoting an understanding of the principles of the invention, reference will now be made to embodiments, some of which are illustrated in the drawings, and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Figure 1:
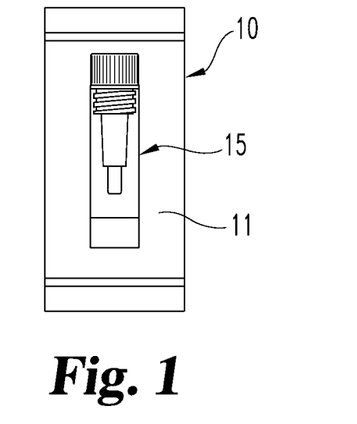
FIG. 1 is a view of an overwrap containing the punch biopsy vial of the present disclosure.
Figure 2:
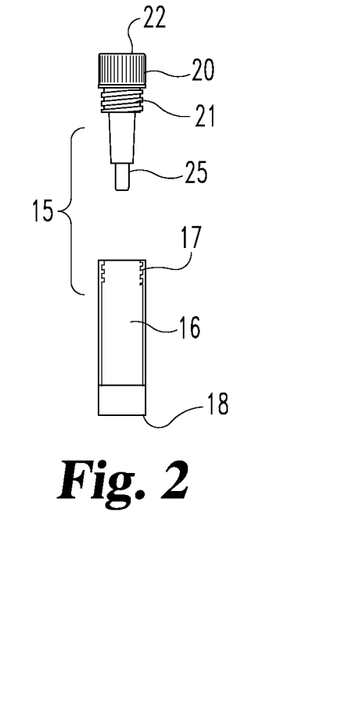
FIG. 2 is an exploded diagram of the vial shown in FIG. 1.
Figure 3:
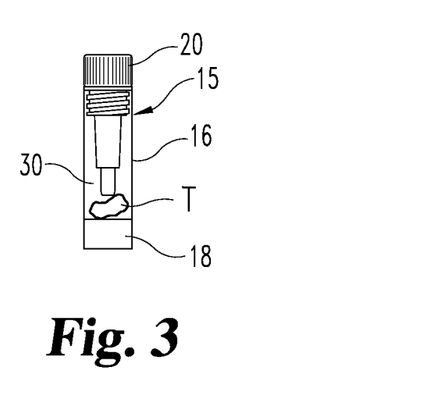
FIG. 3 is a view of the vial shown in FIG. 2 with a tissue sample contained therein.

FIGS. 1-4 show one embodiment of a system useable for tissue extraction procedures in human or animal (veterinary) patients. The tissue extraction system is shown at 10 and it includes a punch biopsy vial 15 that can be provided to any physician in a sterile sealed overwrap 11, as shown in FIG. 1. The overwrap 11 can be, and is preferably, of the type conventionally used for sterile medical devices. The punch biopsy vial 15 includes a container 16 and a cap 20, as shown in FIG. 2 and FIG. 3. In this embodiment, the container 16 has an open mouth 17 at one end and a retrieval port 18 defined at the other end of the container. In another embodiment shown in FIGS. 7-9 and described in greater detail below, a retrieval port 77 similar to retrieval port 18 is included within cap 20. Regardless of position, the retrieval port may have a variety of configurations provided that it can maintain a sterile, sealed, leak-proof closure, while permitting access to withdraw the contents of the container. For instance, the retrieval port 18 may constitute a septum that may be pierced by a syringe, as described herein. Alternatively the port may include a valve arrangement. The retrieval port 18 may be provided with a cover to maintain the sterility of the port until it is desired to access the contents of the container 16.

The cap 20 includes a mating interface 21 adapted to sealingly mate with the mouth 17 of the container 16. The interface may thus be a conventional threaded engagement or Luer-type fitting between the cap and container and may incorporate a seal or gasket between the cap and the container to ensure a fluid-tight seal. The handle 22 of the cap provides a gripping surface to thread the cap onto the container.

In one aspect, the cap 20 incorporates a circular blade 25 that may be configured similar to blades used for a punch biopsy. In one embodiment, the blade is a sterilized stainless steel blade having a diameter of between about 2 mm and about 4 mm. The blade diameter is preferably calibrated for taking a tissue sample from the skin of the patient. The sample should be sufficiently large to ensure a large quantity of viable stem cells, yet not so large as to cause undue trauma to the patient. It has been found that a sample as small as 2 mm provides a sufficient quantity of viable cells. A sample larger than 4 mm yield more cells but the increase in viable cells is of only minimal advantage when culturing the cell sample. On the other hand, the larger diameter lesion left by a skin punch greater than 4 mm has been found to be uncomfortable and unnecessary.

Figure 5:
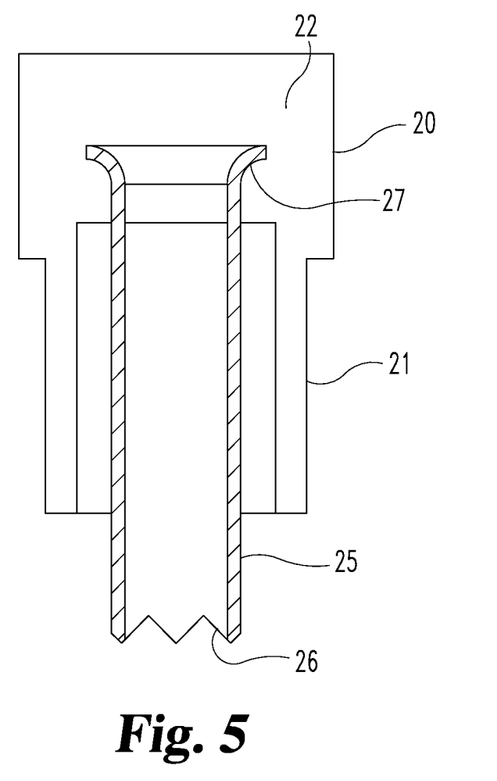
FIG. 5 is an enlarged cross-sectional view of the cap and blade for the vial shown in FIG. 2.

The circular blade 25 is embedded within the cap 20 and concentrically disposed inside the mating interface 21. The blade is solidly anchored within the handle 22 of the cap so that the blade can be rotated by the physician by rotating the cap using the handle. In one embodiment, the blade is mounted within the cap using an over-molding process. The blade may incorporate features to enhance the anchorage of the blade so that it cannot be dislodged from the cap. For instance, as shown in FIG. 5, the blade may include a flared end 27 that is embedded within the handle 22. As further shown in FIG. 5, the blade may include serrations or teeth 26 to facilitate severing the tissue, especially upon rotation of the cap 20. The blade has a length adapted to an appropriate depth for the region of tissue or skin targeted for recover. In one specific embodiment the blade has a height of about 5 mm for an epidermal skin sample.

In one procedure using the tissue extraction system 10, the physician removes the vial 15 from the package 11 and releases the cap 20 from the container 16. The physician then pierces the patient's skin with the blade 25, preferably while rotating the blade. When the blade is removed the tissue sample is trapped within the blade. The cap 20 is then remounted onto the vial 16, as shown in FIG. 3. The tissue sample T may be dislodged into a solution 30 contained within the vial, such as by tapping the cap. It is contemplated that the vial may be provided with the solution as part of the sealed overwrap 11. Alternatively, the solution may be added by the physician, such as from a separate vial provided with the sealed overwrap. However, in order to simplify the procedure it is preferable that the vial be initially filled with the solution 30 so that no problems arise in collecting and transporting the tissue sample T. In one embodiment, the cap 20 may be provided in the overwrap 11 separated from the vial 15. The vial may contain the solution 30 and be provided with a seal that can be broken or penetrated by the blade 25 when the cap is fastened to the vial.

In one aspect of the present disclosure, the solution 30 contained within the vial and into which the tissue sample T is placed, may constitute a variety of compositions depending upon the desired function of the sealed vial shown in FIG. 3. In one embodiment, the solution may be a standard buffered saline solution, with or without other additives depending upon the nature of the tissue and the amount of time that the tissue sample T will remain in the solution before subsequent processing. The solution may also include a chemical preservative that is capable of preserving the tissue sample but is inert to the cells of interest. Various embodiments of solution 30 include any liquid medium commonly known in the art.

In another embodiment, the solution 30 may be a preservative adapted to preserve the tissue and its cells intact. The preservative may be a cryoprotectant so that the vial 15, complete with tissue sample T, may be transported directly to a cryogenic storage facility. The preservative may thus include known permeable cryoprotectant agents, such as dimethyl sulfoxide, ethylene glycol, propylene glycol and glycerol.

In a further alternative, the solution 30 may incorporate enzymes adapted to digest the tissue sample and liberate cells of interest. The enzymatic activity may be modulated by temperature either immediately once the sample is acquired or later at a separate facility. The enzyme can be selected as a function of the tissue being digested, the desired cell, the digestion rate and/or the optimal time of digestion. In the latter case, the digestion time may be controlled by shipping the sealed vial in a shipping container having a timed cooling feature that is activated at an appropriate time to slow the enzymatic activity. One suitable enzyme is ACCUTASE® sold by Life Technologies Corp dba Invitrogen Corp.

Figure 4:
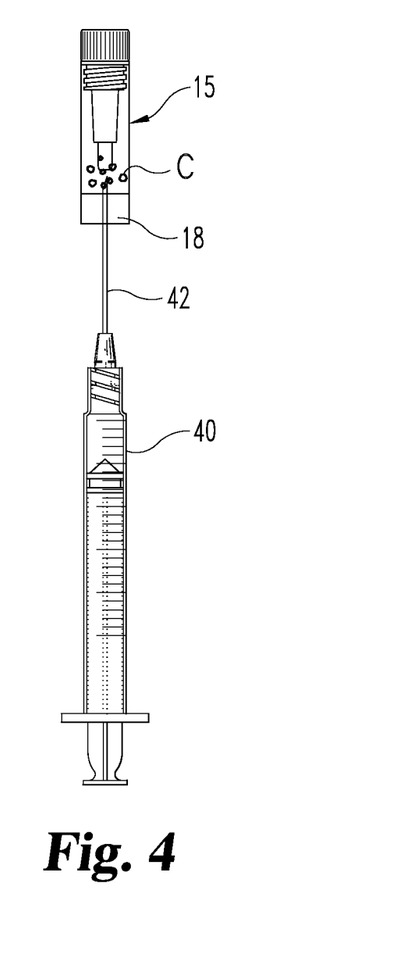
FIG. 4 is a diagram of a step for withdrawing cells from the vial shown in the prior figures.

In this embodiment, it is thus contemplated that the solution will digest the tissue to liberate cells C of interest, as shown in FIG. 4. The cells C may be removed from the vial 15 using a hypodermic needle 42 and syringe 40. The needle penetrates the sealed end 18 of the vial in a known fashion. The suspended cells are withdrawn into the syringe to be taken to other processing.

Figure 6:
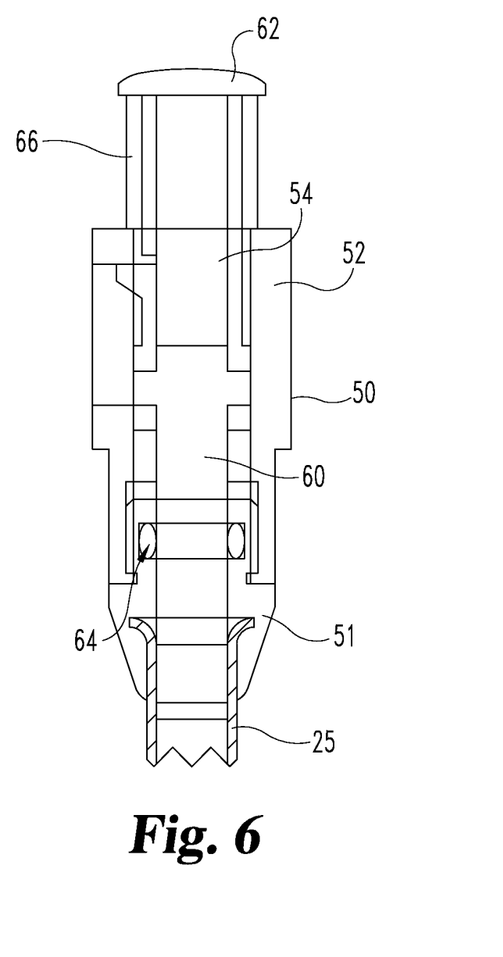
FIG. 6 is a cross-sectional view of a modified cap for the vial shown in the prior figures.

In order to facilitate dislodging the tissue sample into the vial, a plunger arrangement may be provided as illustrated in FIG. 6. The cutting blade 25 may be the same as described above, mounted within the mating interface 51 of the cap 50. As shown in FIG. 6, the mating interface may be in the form of a tapered stopper, or maybe the threaded interface described above. The cap 50 is longer than the cap 20, including a longer handle 52. The cap provides a passageway 54 through which a plunger 60 extends. The plunger 60 includes an end 62 that is depressed to push the plunger down through the blade 25 to dislodge the tissue sample from within the blade. The plunger may include a seal 64, such as on O-ring, disposed between the plunger and the passageway 54. In addition, a spring 66 may be provided between the end 62 and the handle 52 to bias the plunger away from the blade.

Figure 7:
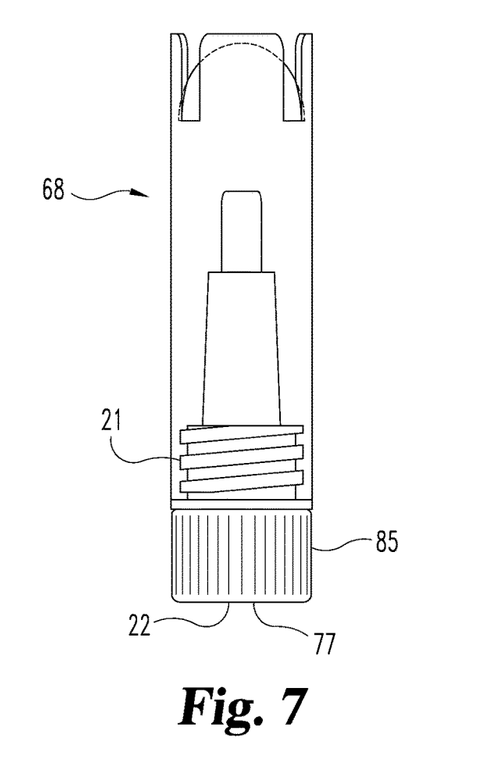
FIG. 7 is another embodiment of the punch biopsy vial shown in FIGS. 1-4.
Figure 8:
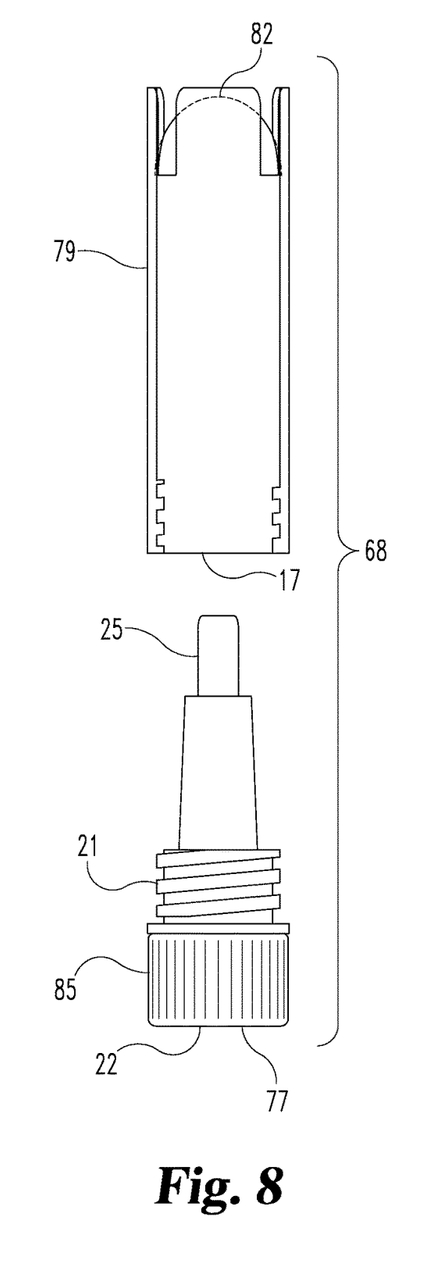
FIG. 8 is an exploded diagram of the vial shown in FIG. 7.
Figure 9:
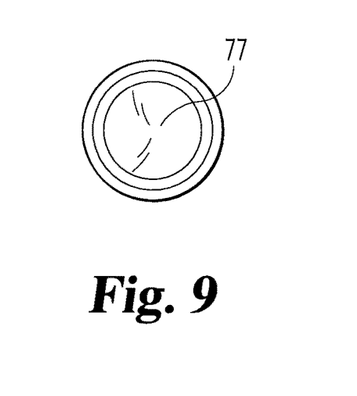
FIG. 9 is end view of the distal end of the vial shown in FIG. 7.

Another embodiment of the punch biopsy vial is show in FIG. 7-FIG. 9 at 68 which is similar to vial 15. Biopsy vial 68 includes a container 79 similar to container 16 except that in this embodiment, container 79 has an open mouth 17 at one end and closed end 82 defined at the other end of container 79 rather than a retrieval port. A retrieval port 77 similar in all respects to retrieval port 18 described above is incorporated into a cap 85 which includes the embodiments of handle 22 and mating region 21 described above. Cap 85 is constructed similarly to the embodiments of cap 20 described above and includes a circular blade 25 that is positionable inside container 79 as shown in FIG. 7. One embodiment of retrieval port 77 is shown in FIG. 9 as a septum configured within the central area of cap 85 such that a needle or other similar instrument can be inserted through the septum into container 79 to retrieve the contents of the container similar to what is shown in FIG. 4 with respect to the previous embodiment.

Figure 10:
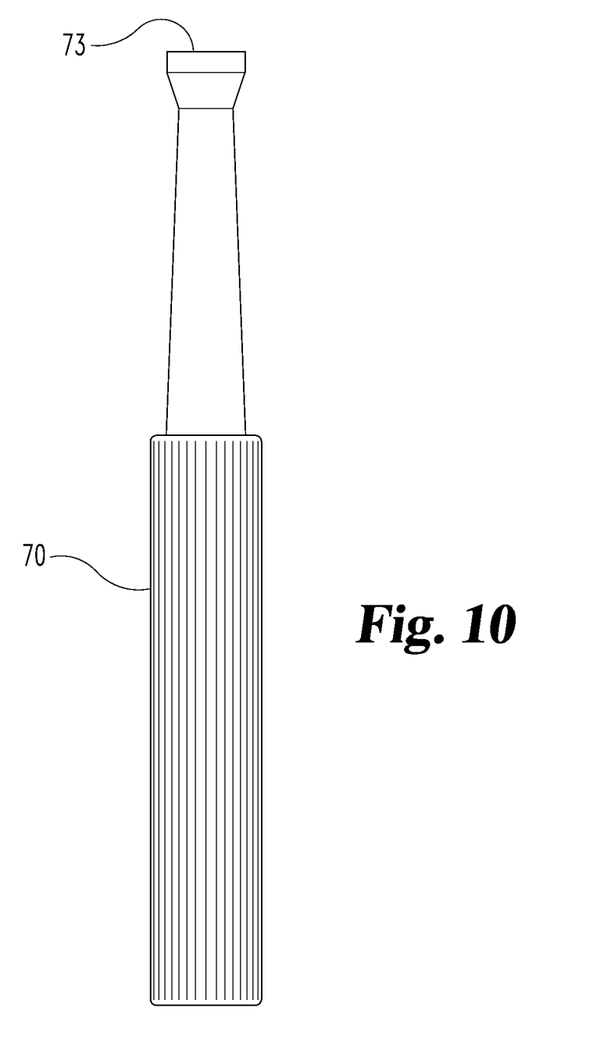
FIG. 10 is a side view of a handle for use with the biopsy vials shown in FIG. 1-9.
Figure 11:
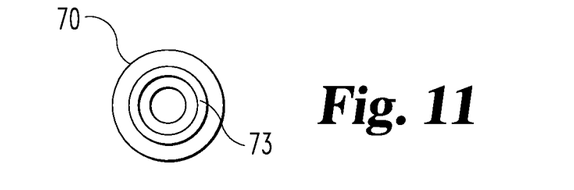
FIG. 11 is an end view of the distal end of the handle shown in FIG. 10.

Also shown in FIG. 10 and FIG. 11 is one embodiment of an elongate handle 70 that may be used in conjunction with the embodiments of the punch biopsy vial described above. The handle has an elongate tubular shape with a contact region 73 at the distal end which in one embodiment can be pressed against the cap of the biopsy vial to aid in steadying blade 25 during a tissue extraction or other procedure. Contact region 73, in one embodiment, press fits into a corresponding detent, notch, or similar receiving region in the cap to firmly steady handle 70 during the procedure. Handle 70 may also be secured to the cap by screw threads at or near the contact region 73 that correspond with similar threads in the cap. Other nondestructible attachment means may be used as well such as pins, snaps, and the like. In another embodiment, handle 70 is formed as part of the vial cap and designed to be broken or otherwise separated from the cap and discarded after the tissue extraction procedure has been completed. In still another embodiment, handle 70 is formed with the cap as a single disposable unit. Other forms of attaching handle 70 to the vial cap include thermal bonding, adhesive bonding, bonding by chemical reaction, or other non-detachable permanent means.

The uses of the terms "a" and "an" and "the" and similar references in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. In addition, all references cited herein are indicative of the level of skill in the art and are hereby incorporated by reference in their entirety.

LISTING OF CERTAIN EMBODIMENTS

1. A tissue extraction vial comprising:
    a container having a mouth and a retrieval port, the retrieval port also having a closure configured to permit access into the container;
    a cap, and
    a blade configured to capture a tissue sample;
    wherein the blade is attached to the cap;
    wherein the cap is adapted to mate with the mouth, and;
    wherein the cap is adapted to sealingly mate with the mouth of the container.
2. The tissue extraction vial of embodiment 1 wherein the blade defines an internal lumen.
3. The tissue extraction vial of embodiment 2 wherein the blade is circular.
4. The tissue extraction vial of embodiment 3 wherein the circular blade has a diameter between about 2 mm and about 4 mm.
5. The tissue extraction vial as in any preceding embodiment wherein the blade is made of stainless steel.
6. The tissue extraction vial as in any preceding embodiment wherein the blade has a height of about 5 mm.
7. The tissue extraction vial of any preceding embodiment further comprising:
    a plunger, wherein the plunger is configured to dislodge the tissue sample.
8. The tissue extraction vial as in any preceding embodiment wherein the closure is a septum that can be pierced by a needle.
9. The tissue extraction vial as in any preceding embodiment further comprising a liquid medium inside the container.
10. The tissue extraction vial as in embodiment 9 wherein the liquid medium is a solution.
11. The tissue extraction vial as in embodiment 9 or 10 further comprising a chemical preservative capable of preserving the tissue sample inside the container.
12. The tissue extraction vial as in embodiment 9 or 10 further comprising a preservative with a permeable cryoprotectant agent inside the container.
13. The tissue extraction vial as in embodiment 9 or 10 further comprising one of the following preservatives inside the container: dimethyl sulfoxide, ethylene glycol, propylene glycol, or glycerol.
14. The tissue extraction vial as in embodiment 9 or 10 further comprising one of the following enzymes adapted to digest a tissue sample inside the container.
15. The tissue extraction vial of any preceding embodiment wherein the retrieval port is at one end of the container, and the mouth is at another end of the container.
16. A method of extracting tissue comprising the steps of:
    acquiring a tissue extraction device comprising:
        a container having a mouth and a retrieval port, the retrieval port also having a closure configured to permit access into the container;
        a cap, and
        a blade configured to capture a tissue sample;
        wherein the blade is attached to the cap;
        wherein the cap is adapted to mate with the mouth, and;
        wherein the cap is adapted to sealingly mate with the mouth of the container.
    obtaining a tissue sample using the blade;
    placing the tissue sample inside the container, and;
    mating the cap to the container mouth.
17. The method of extracting tissue in embodiment 14 wherein the tissue extraction device has a liquid medium inside the container.
18. The method of extracting tissue in embodiment 16 wherein the liquid medium is a solution.
19. The method of extracting tissue in embodiment 16 or 17 wherein a chemical preservative adapted to preserve the tissue sample and cells is also inside the container.
20. The method of extracting tissue in embodiment 16 or 17 wherein a preservative that includes a permeable cryoprotectant agent is also in the container.
21. The method of extracting tissue in embodiment 16 or 17 wherein one of the following preservatives is also inside the container: dimethyl sulfoxide, ethylene glycol, propylene glycol, or glycerol.
22. The method of extracting tissue in embodiment 14 comprising the additional steps of:
    acquiring a tissue extraction device wherein the solution in the inner void incorporates enzymes adapted to digest the tissue sample to liberate cells from the tissue sample;
    extracting the cells through the retrieval port.
23. A tissue extraction vial comprising:
    a container;
    a cap for the container;
    a blade configured to capture a tissue sample, the blade attached to the cap; and
    a needle-penetrable septum adapted to provide access into the container.
24. The vial of embodiment 23 wherein the blade is receivable within the container when the cap is mated to the container.
25. A cap assembly for capping a container, comprising:
    a cap matable with a container;
    a blade configured to capture a tissue sample, the blade attached to the cap; and
    a needle-penetrable septum mounted in the cap and adapted to provide access through the cap into the container when the cap is mated to the container.
26. The cap assembly of embodiment 25, wherein the blade defines an inner lumen having a longitudinal axis, and wherein at least a portion of the septum is aligned with said longitudinal axis.

What is claimed is:
1. A tissue extraction vial comprising:
    a container;
    a cap for the container;
    a blade configured to capture a tissue sample, the blade attached to the cap; and
    a needle-penetrable septum adapted to provide access into the container;
    wherein an end of the blade extends outside a periphery of the cap so as to be exposed for capturing a tissue sample;

wherein the blade has a length extending outside the periphery of the cap; and wherein the length is entirely within the container without the blade passing through the needle-penetrable septum when the cap is mated to the container.

2. The vial of claim 1 wherein the cap comprises the needle-penetrable septum.

3. The vial of claim 1 wherein the needle-penetrable septum is mounted in the container.

4. The vial of claim 3 wherein the cap is matable to the first end of the container and the needle-penetrable septum is mounted at the second end of the container.

5. The vial of claim 1 wherein the punch-biopsy blade defines an inner lumen having a longitudinal axis, and wherein at least a portion of the septum is aligned with said longitudinal axis.

6. The vial of claim 1 wherein the cap comprises a threaded portion arranged to engage a threaded portion of the container when the cap is mated to the container.

7. The vial of claim 1 wherein the blade is a punch-biopsy blade.

8. A tissue extraction vial comprising:

a container;

a cap for the container;

a punch-biopsy blade configured to capture a tissue sample, the punch-biopsy blade attached to the cap; and a needle-penetrable septum defining an outer wall of the tissue extraction vial and adapted to provide access into the container when the cap is mated to the container;

wherein the punch-biopsy blade defines an inner lumen extending along a length of the punch-biopsy blade, the inner lumen having an open, first end and a closed, second end;

wherein the cap comprises a threaded portion arranged to engage a threaded portion of the container when the cap is mated to the container; and wherein when the threaded portion of the cap is engaged with the threaded portion of the container, the open, first end of the inner lumen is positioned within the container without the inner lumen passing through the needle-penetrable septum.

\* \* \* \* \*

UNITED STATES PATENT AND TRADEMARK OFFICE
CERTIFICATE OF CORRECTION

PATENT NO. : 10,653,397 B2  
APPLICATION NO. : 15/388145  
DATED : May 19, 2020  
INVENTOR(S) : Erik John Woods

Page 1 of 1

It is certified that error appears in the above-identified patent and that said Letters Patent is hereby corrected as shown below:

In the Claims

In Column 7, Line 10, Claim 4, delete "to the" and insert --to a--.

Signed and Sealed this  
Tenth Day of September, 2024

Katherine Kelly Vidal  
*Director of the United States Patent and Trademark Office*